(12) United States Patent
Wang et al.

(10) Patent No.: US 8,243,071 B2
(45) Date of Patent: Aug. 14, 2012

(54) MODELING AND RENDERING OF HETEROGENEOUS TRANSLUCENT MATERIALS USING THE DIFFUSION EQUATION

(75) Inventors: Jiaping Wang, Beijing (CN); Xin Tong, Beijing (CN); Stephen S. Lin, Beijing (CN); Baining Guo, Beijing (CN); Heung-Yeung Shum, Beijing (CN); Zhouchen Lin, Beijing (CN)

(73) Assignee: Microsoft Corporation, Redmond, WA (US)

(*) Notice: Subject to any disclaimer, the term of this patent is extended or adjusted under 35 U.S.C. 154(b) by 992 days.

(21) Appl. No.: 12/072,925

(22) Filed: Feb. 29, 2008

(65) Prior Publication Data

US 2009/0219287 A1    Sep. 3, 2009

(51) Int. Cl.
*G06T 15/00* (2011.01)
*G06T 15/60* (2006.01)
*G06K 9/00* (2006.01)

(52) U.S. Cl. ........................ 345/426; 382/108
(58) Field of Classification Search .................. 345/426; 356/446; 382/108, 286
See application file for complete search history.

(56) References Cited

U.S. PATENT DOCUMENTS

| | | | |
|---|---|---|---|
| 4,662,222 A * | 5/1987 | Johnson | 73/602 |
| 6,420,709 B1 | 7/2002 | Block et al. | |
| 7,019,744 B2 * | 3/2006 | Anderson | 345/424 |
| 7,190,461 B2 | 3/2007 | Han et al. | |
| 7,443,394 B2 * | 10/2008 | Anderson et al. | 345/424 |
| 7,859,530 B2 * | 12/2010 | Tomson et al. | 345/424 |
| 7,864,176 B2 * | 1/2011 | Planck et al. | 345/424 |
| 2001/0040997 A1 * | 11/2001 | Tsap et al. | 382/154 |
| 2003/0231175 A1 * | 12/2003 | Pfister et al. | 345/419 |
| 2004/0150642 A1 * | 8/2004 | Borshukov et al. | 345/426 |
| 2004/0227761 A1 * | 11/2004 | Anderson et al. | 345/473 |
| 2005/0068537 A1 * | 3/2005 | Han et al. | 356/446 |
| 2006/0028468 A1 * | 2/2006 | Chen et al. | 345/424 |
| 2006/0214931 A1 * | 9/2006 | Snyder et al. | 345/426 |
| 2006/0227137 A1 * | 10/2006 | Weyrich et al. | 345/426 |
| 2006/0290719 A1 * | 12/2006 | Tong et al. | 345/694 |
| 2006/0293597 A1 * | 12/2006 | Johnson et al. | 600/437 |
| 2007/0132759 A1 * | 6/2007 | Mallick et al. | 345/426 |
| 2007/0229502 A1 * | 10/2007 | Tong et al. | 345/426 |
| 2007/0285422 A1 * | 12/2007 | Nayar et al. | 345/426 |
| 2007/0286468 A1 * | 12/2007 | Joshi et al. | 382/131 |
| 2008/0143720 A1 * | 6/2008 | Elmquist | 345/426 |
| 2008/0255812 A1 * | 10/2008 | Hery | 703/2 |
| 2008/0285827 A1 * | 11/2008 | Meyer et al. | 382/131 |
| 2009/0213120 A1 * | 8/2009 | Nisper et al. | 345/426 |
| 2009/0226049 A1 * | 9/2009 | Debevec et al. | 382/118 |

OTHER PUBLICATIONS

Jensen et al.; A Practical Model for Subsurface Light Transport; 2001; ACM, SIGGRAPH 2001; pp. 511-518.*

(Continued)

*Primary Examiner* — David T Welch
(74) *Attorney, Agent, or Firm* — Lee & Hayes, PLLC

(57) ABSTRACT

An exemplary method includes providing image data for an illuminated physical sample of a heterogeneous translucent material, determining one or more material properties of the material based in part on a diffusion equation where one of the material properties is a diffusion coefficient for diffusion of radiation in the material and where the determining includes a regularization term for the diffusion coefficient, mapping the one or more material properties to a virtual object volume, assigning virtual illumination conditions to the virtual object volume, and rendering the virtual object volume using the virtual illumination conditions as a boundary condition for a system of diffusion equations of the virtual object volume. Other methods, devices and systems are also disclosed.

18 Claims, 10 Drawing Sheets

EXEMPLARY TECHNIQUE 400
(CONJUGATE GRADIENT BASED ALGORITHM)

410 Set initial material properties: $\vec{\kappa}_0, \vec{\mu}_0$

420 Set initial search direction: $\vec{d}_0 = -\vec{z}(\kappa_0, \mu_0)$ and $\vec{p}_0 = \vec{d}_0$ 430 Repeat following steps until $f_M < \varepsilon$ 431 Compute gradient $\vec{z}(\kappa_t, \mu_t) = \left( \frac{df_M(\vec{\kappa}, \vec{\mu})}{d\kappa(x)}, \frac{df_M(\vec{\kappa}, \vec{\mu})}{d\mu(x)} \right)$ 432 Set $p_t = -\vec{z}(\kappa_t, \mu_t)$ 433 Update search direction $\vec{d}_t = \vec{p}_t + \beta \cdot \vec{d}_{t-1}$, $$\beta = \max\left( \frac{\vec{p}_t^T (\vec{p}_t - \vec{p}_{t-1})}{\vec{p}_{t-1}^T \vec{p}_{t-1}}, 0 \right)$$

434 Golden section search $\lambda'$ by $\min_{\lambda'} \left[ f_M \left( (\vec{\kappa}_t, \vec{\mu}_t) + \lambda' \vec{d}_t \right) \right]$ 435 Update solution $(\vec{\kappa}_{t+1}, \vec{\mu}_{t+1}) = (\vec{\kappa}_t, \vec{\mu}_t) + \lambda' \vec{d}_t$

OTHER PUBLICATIONS

Jensen et al.; A Rapid Hierarchical Rendering Technique for Translucent Materials; Jul. 2002; ACM, SIGGRAPH 2002; vol. 21, Issue 3; pp. 576-581.*

Donner et al.; Light Diffusion in Multi-layered Translucent Materials; Jul. 2005; ACM, SIGGRAPH 2005; vol. 24, Issue 3; pp. 1032-1039.*

Kong, et al., "An Efficient Caching Technique for Rendering Translucent Materials", at <<http://cggmwww.csie.nctu.edu.tw/research/KLC05.pdf>>, The Eurographics Association, 2005, pp. 8.

Mertens, et al., "Efficient Rendering of Local Subsurface Scattering", available at least as early as Aug. 2, 2007, at <<http://people.csail.mit.edu/kautz/publications/localsssPG03.pdf>>, pp. 8.

Mertens, et al., "Interactive Rendering of Translucent Deformable Objects", at <<http://delivery.acm.org/10.1145/890000/882423/p130-mertens.pdf?key1=882423&key2=1588595811&coll=GUIDE&dl=GUIDE&CFID=25558943&CFTOKEN=87300288>>, Eurographics Symposium on Rendering, 2003, pp. 12.

Shopf, "Interactive Rendering of Heterogeneous Translucent Objects", at <<http://www.csee.umbc.edu/~olano/papers/theses/Shopf2007.pdf>>, 2007, pp. 63.

Stam, "Multiple Scattering as a Diffusion Process", available at least as early as Aug. 2, 2007, at <<http://www.dgp.toronto.edu/people/stam/reality/Research/pdf/egwr95.pdf>>, pp. 11.

Tong, et al., "Modeling and Rendering of Quasi-Homogeneous Materials", available at least as early as Aug. 2, 2007, at <<https://research.microsoft.com/users/xtong/quasi.pdf>>, pp. 8.

* cited by examiner

EXEMPLARY TECHNIQUE 300
PHYSICAL MODEL 310
FORWARD PROBLEM: DIFFUSION PROCESS 320
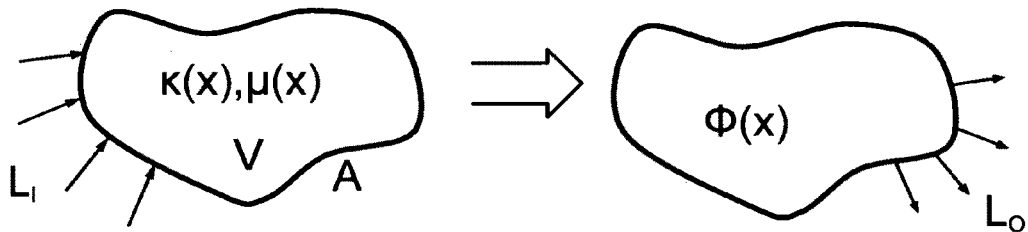
INVERSE PROBLEM: MATERIAL PROPERTIES 330
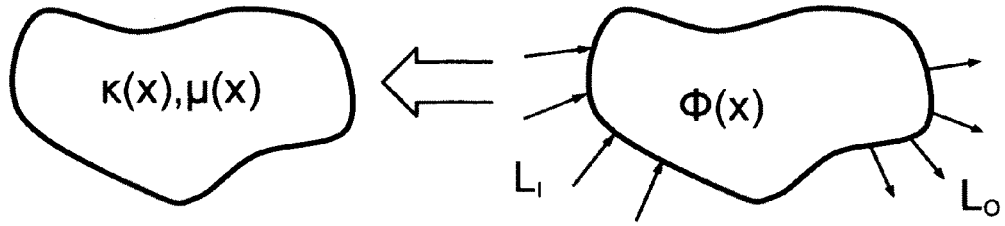
FIG. 3

EXEMPLARY TECHNIQUE 400
(CONJUGATE GRADIENT BASED ALGORITHM)

410 Set initial material properties: $\vec{\kappa}_0, \vec{\mu}_0$

420 Set initial search direction: $\vec{d}_0 = -\vec{z}(\kappa_0, \mu_0)$ and $\vec{p}_0 = \vec{d}_0$ 430 Repeat following steps until $f_M < \varepsilon$ 431 Compute gradient $\vec{z}(\kappa_t, \mu_t) = \left( \frac{df_M(\vec{\kappa},\vec{\mu})}{d\kappa(x)}, \frac{df_M(\vec{\kappa},\vec{\mu})}{d\mu(x)} \right)$ 432 Set $p_t = -\vec{z}(\kappa_t, \mu_t)$ 433 Update search direction $\vec{d}_t = \vec{p}_t + \beta \cdot \vec{d}_{t-1}$, $$\beta = \max\left( \frac{\vec{p}_t^T (\vec{p}_t - \vec{p}_{t-1})}{\vec{p}_{t-1}^T \vec{p}_{t-1}}, 0 \right)$$

434 Golden section search $\lambda'$ by $\min_{\lambda'} \left[ f_M\left( (\vec{\kappa}_t, \vec{\mu}_t) + \lambda' \vec{d}_t \right) \right]$ 435 Update solution $(\vec{\kappa}_{t+1}, \vec{\mu}_{t+1}) = (\vec{\kappa}_t, \vec{\mu}_t) + \lambda' \vec{d}_t$

FIG. 4

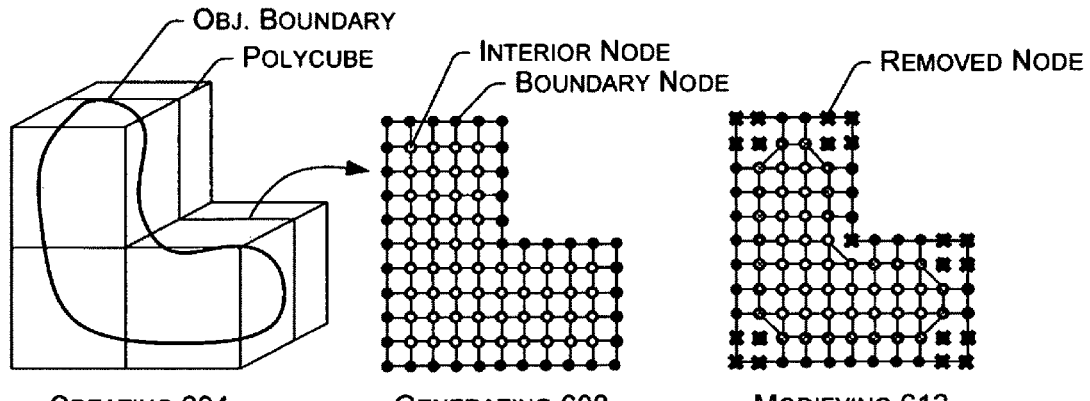
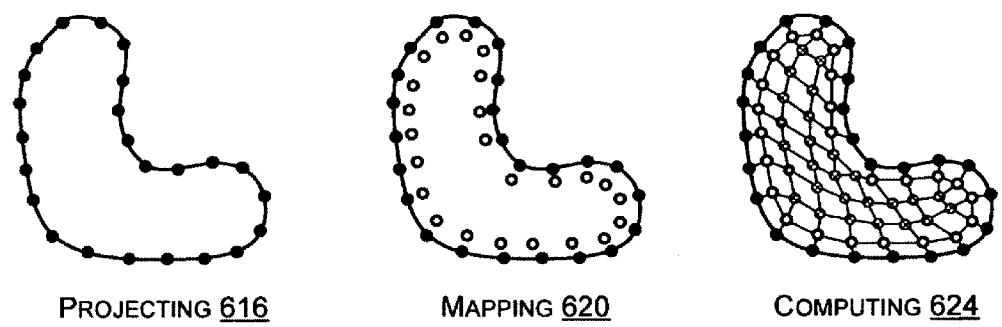
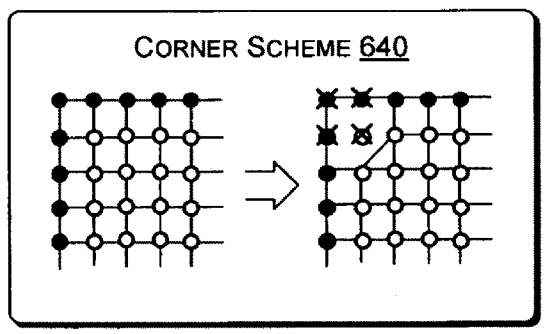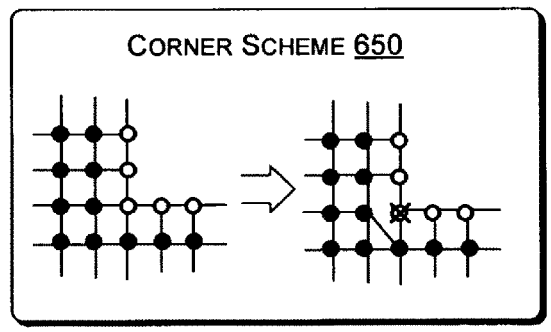
FIG. 6

MODELING AND RENDERING OF HETEROGENEOUS TRANSLUCENT MATERIALS USING THE DIFFUSION EQUATION

BACKGROUND

Many materials in the real world exhibit a complex appearance that arises from subsurface scattering of light. For heterogeneous translucent objects, the light transport within the material volume is determined by its geometry, the optical properties of its constituent elements, and the spatial distribution of these elements in the volume. Because of the complex effects of these various factors on subsurface scattering, models of these materials have been challenging to acquire from real objects and to render in real time. Furthermore, computational costs and/or modeling deficiencies have made interactive editing of material properties a difficult problem. As described herein, various exemplary systems, methods, etc., provide for modeling and/or rendering of heterogeneous translucent material.

SUMMARY

An exemplary method includes providing image data for an illuminated physical sample of a heterogeneous translucent material, determining one or more material properties of the material based in part on a diffusion equation where one of the material properties is a diffusion coefficient for diffusion of radiation in the material and where the determining includes a regularization term for the diffusion coefficient, mapping the one or more material properties to a virtual object volume, assigning virtual illumination conditions to the virtual object volume, and rendering the virtual object volume using the virtual illumination conditions as a boundary condition for a system of diffusion equations of the virtual object volume. Other methods, devices and systems are also disclosed.

DESCRIPTION OF DRAWINGS

Non-limiting and non-exhaustive examples are described with reference to the following figures:

FIG. 3 is a diagram of an exemplary technique for modeling heterogeneous translucent materials;

FIG. 4 is a set of equations for an exemplary conjugate gradient based technique;

FIG. 6 is a diagram of an exemplary scheme for generating a polygrid to model a virtual object;

DETAILED DESCRIPTION

Figure 1:
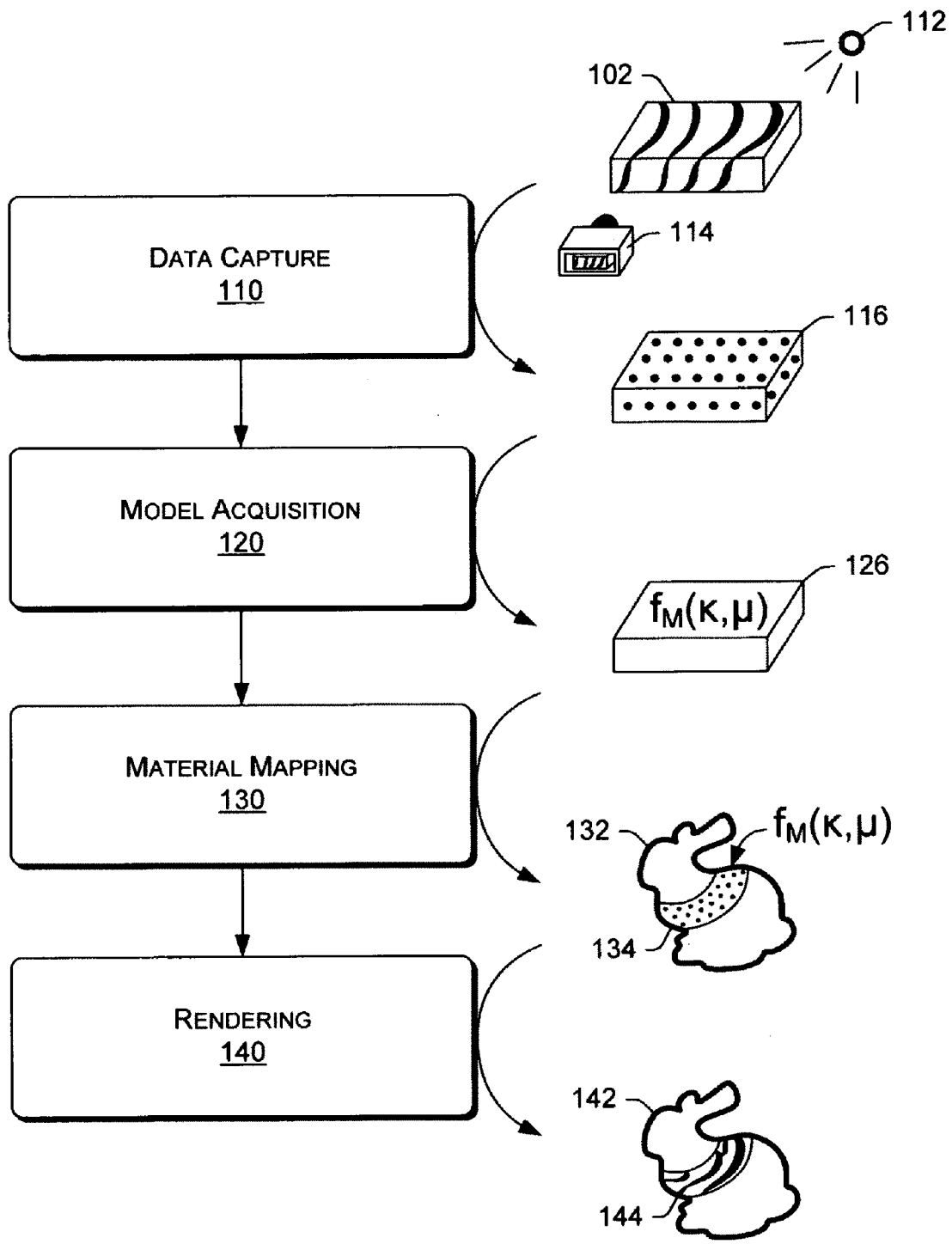
FIG. 1 is a diagram of an exemplary method for modeling and rendering of heterogeneous translucent material.

Various exemplary methods, devices, systems, etc., described herein pertain to creating artificial visual objects and/or scenes. An exemplary method includes acquiring data from an illuminated physical sample, determining material properties of the physical sample based on the acquired data, mapping the material properties to at least a portion of an object and rendering the object to provide for a visual display of the object where the object exhibits characteristics of the physical sample.

As described herein, various exemplary techniques pertain to modeling and rendering of heterogeneous translucent materials that enable acquisition from measured samples, interactive editing of material attributes, and real-time rendering. In various examples, the materials are assumed to be optically dense such that multiple scattering can be approximated by a diffusion process described by the diffusion equation.

An exemplary process for modeling heterogeneous materials includes an algorithm for acquiring material properties from appearance measurements by solving an inverse diffusion problem. As such an inverse problem can be ill-conditioned, the process optionally incorporates a regularizer (i.e., to handle ill-conditioned situations), an adjoint method to dramatically reduce computational cost, and/or a hierarchical GPU implementation to reduce computational cost.

To display an object with known material properties, an exemplary algorithm allows for rendering by solving the diffusion equation with a boundary condition defined by a given illumination environment. In various examples, the exemplary algorithm is centered around object representation by a polygrid, a grid with regular connectivity and an irregular shape, which facilitates the solution of the diffusion equation in arbitrary volumes. Because of the regular connectivity, the exemplary rendering algorithm can be implemented on a GPU for real-time performance. Various examples demonstrate exemplary methods for capturing materials from physical samples and performing real-time rendering and editing with these materials.

As mentioned, various techniques pertain to modeling and rendering of heterogeneous translucent materials. Examples demonstrate acquisition of data from physical samples, interactive editing of material attributes, and real-time rendering. For rendering, material can be represented as a discretized volume (e.g., volume elements or voxels) in which spatially-variant absorption and diffusion coefficients are associated with each voxel. In various examples, multiple scattering is accounted for where the material is assumed to be optically dense such that subsurface scattering becomes isotropic and can be approximated by a diffusion process.

For modeling heterogeneous materials, an exemplary algorithm allows for recovering a material model from appearance measurements by solving an inverse diffusion problem. For a given distribution of spatially-variant absorption and diffusion coefficients, the corresponding diffusion process that generates the material appearance can be expressed as a partial differential equation, defined over the volumetric elements, with a boundary condition given by a lighting environment.

A process of acquiring a volumetric model from a material sample involves an inverse diffusion problem in which a search for a distribution of spatially-variant absorption and diffusion coefficients such that a corresponding diffusion process generates the material appearance that is consistent with the measured surface appearance in captured images.

Through an optimization or solution, the process aims to generate the material appearance that is most consistent.

As described herein, in various examples images record an actual material sample where a solution to the inverse diffusion problem is assumed with a high degree of certainty to exist. However, such inverse problems, are known to be ill-posed, since a range of different volumetric models may have indistinguishable surface appearances. In other words, different "interiors" can produce visually indistinguishable surface appearance for an object. Consequently, the diffusion equations and image measurements define, for a material sample, a group of solutions. Since all solutions correspond to the same visual appearance, any solution from this group provides a valid volumetric appearance model of the given material.

Finding a solution to the inverse diffusion problem is challenging due to the nature of the inverse problem and the large number of variables involved. The inverse diffusion problem is usually solved with an iterative optimization procedure, in which each iteration requires an expensive gradient evaluation. For a volume with elements on an $n^3$ grid, this gradient evaluation involves $n^3 \times M$ light diffusion computations, where M is the number of image measurements. The inverse diffusion problem is also ill-conditioned numerically, which presents convergence problems for the iterative solver.

As described herein, to ensure stable convergence, an exemplary method incorporates a regularizer on the diffusion coefficients and includes an effective initialization that assigns uniform diffusion coefficients among the voxels. In various examples, an adjoint method, widely used in optimal control for gradient computation, is used to dramatically reduce the cost of the gradient evaluation down to 2M light diffusion computations. With such schemes and a GPU implementation of the diffusion computation, various examples demonstrate that finding a solution of the inverse diffusion problem becomes feasible for volumes of moderate size.

Also described herein, is an exemplary algorithm for rendering a volumetric model with known material properties that includes solving a diffusion equation whose boundary condition is defined by some stated illumination conditions, which may be varied (e.g., spatially, over time, etc.).

With respect to solving a formulated set of equations (e.g., diffusion equation and associated boundary condition or conditions) for 3D volumes of arbitrary shape, an exemplary technique includes a polygrid and an finite difference method (FDM). Such an algorithm is centered around the polygrid representation, which facilitates the solution of the light diffusion equation in arbitrary volumes. A polygrid is a grid with regular connectivity and an irregular shape for a close geometric fit without fine sampling. Regular connectivity allows for development of a hierarchical GPU implementation of an exemplary rendering algorithm for real-time performance.

Construction of a polygrid on an arbitrary 3D object is described below along with a technique for evaluating diffusion equations defined among irregular intervals of polygrid nodes. With such a technique, models of various materials can be readily captured and interactively transformed with adjustments of scattering properties. An exemplary system allows for flexible use of real appearance data provides designers a valuable tool for creating realistic objects with the visual features of heterogeneous translucent materials. As described herein, an exemplary system supports real-time rendering and editing of such volumes.

FIG. 1 shows an exemplary method 100 for modeling and rendering material. The method 100 commences in a data capture step 110. As shown in FIG. 1, a material sample 102 is illuminated by a light source 112 and images of the material sample 102 are captured by a sensor device 114 (e.g., a camera). For purposes of illustration, the material sample 102 includes a "zebra" like pattern that extends throughout the volume of the sample. In the example of FIG. 1, the device 114 captures data that can be analyzed by a computing device to associate data points with coordinates of the material sample 116.

According to the method 100, a model acquisition step 120 forms a model 126 of the material sample 102 based at least in part on the captured data 116. In the example of FIG. 1, the model acquisition step 120 determines volumetric material properties (e.g., the properties κ and μ).

Once one or more materials properties are known, a material mapping step 130 can map the material to a virtual object 132 as indicated by the band 134 on the virtual rabbit object 132. In the example of FIG. 1, the band 134 may be a volumetric slice, an annulus, etc., in the virtual object 132. In other words, the band 134 can have any dimension or thickness in the virtual object 132. Indeed, the band 134 may be an interior band that resides below the surface of the virtual object 132.

After mapping, a rendering step 140 renders the material per the one or more properties to generate a visual representation of the virtual object 142 that includes a visual representation of the material 144. The rendering step 140 normally relies on illumination. The illumination may be visible or other "radiation" that can permeate the material. The illumination may be from a single source, multiple sources, multiple wavelengths, etc.

Figure 2:
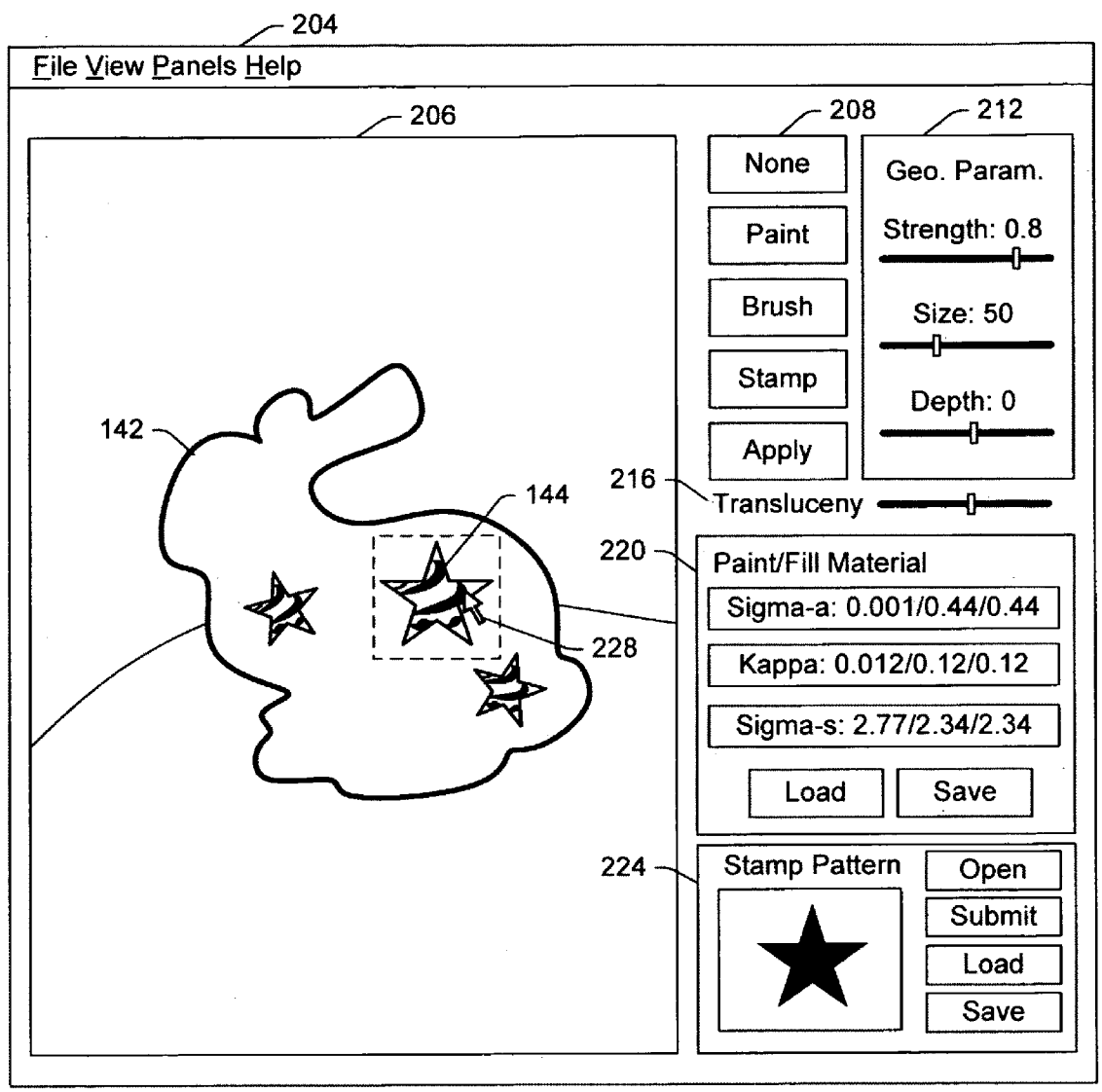
FIG. 2 is a diagram of an exemplary graphical user interface (GUI) for editing graphics with heterogeneous translucent materials.

FIG. 2 shows an exemplary graphical user interface (GUI) 200 for creating virtual objects and/or virtual scenes. The GUI 200 can be used to perform at least part of the mapping step 130 of the method 100 of FIG. 1. The GUI 200 can be used to perform at least part of the rendering step 140 of the method 100 of FIG. 1.

In the example of FIG. 2, the GUI 200 includes various commands in a command field 204, a drawing field 206, a command buttons field 208, a geometric parameters field 212 (e.g., with slider controls), a translucency control 216 (e.g., with a slider control), a paint/fill material field 220, and a stamp pattern field 224.

A user can navigate a cursor 228 in the drawing field 206. For example, a user can position the cursor 228 on the virtual rabbit object 142 to "paint" a material 144 using a stamp pattern where the stamp pattern maps certain material properties to the virtual rabbit object 142. As indicated, a user may change the stamp pattern using controls in the stamp pattern field 224 and select a material using controls in the paint/fill material field 220. The geometric parameters field 212 can be used to control "strength" of the mapped material, size of the mapped material and depth of the mapped material.

As the object and/or scene that appears in the drawing field 206 is virtual, parameters such as translucency can be adjusted (e.g., per the translucency control 216). For example, white quartz from a specific site in Nevada may be selected as the material. However, once mapped to the virtual object 142, the user may desire a more translucent version of this white quartz. Such a desire may be met using the control of the translucency field 216.

A more detailed description of various exemplary techniques follows along with some examples. FIG. 3 shows an exemplary technique 300 that includes a physical model 310 for diffusion of light in a material, a forward problem for a diffusion process 320 and an inverse problem for a diffusion process for determining one or more material properties 330.

As indicated in the physical model 310, subsurface scattering of light in a heterogeneous material can be quite complex and stochastic and determined by object geometry, material properties and distribution of the light in the object volume. In the forward problem 320, let the object interior be volume V and the object surface be A. The outgoing radiance $L(x_o,\omega_o)$ at a surface point $x_o$ in direction $\omega_o$ may be computed by integrating the incoming radiance $L(x_o,\omega_o)$ from all incident directions $\omega_o$ and points $x_i$ on surface A:

$$L_o(x_o,\omega_o) = \int_A \int_{\Omega^2} S(x_i,\omega_i,x_o,\omega_o) L_i(x_i,\omega_i)(n\cdot\omega_i) d\omega_i dA(x_i)$$

where n is the surface normal at $x_i$ and $S(x_i,\omega_i,x_o,\omega_o)$ is the BSSRDF. The outgoing radiance can be divided into single- and multiple-scattering components:

$$L_o(x_o,\omega_o) = L_s(x_o,\omega_o) + L_m(x_o,\omega_o).$$

The single-scattering component $L_s(x_o,\omega_o)$ accounts for light that interacts exactly once with the medium before exiting the volume, and may be evaluated by integrating the incident radiance along the refracted outgoing ray. An exemplary technique focuses on multiple scattering and uses a highly simplified single scattering term that assumes scattering to be isotropic and occurring only at surface points $x_o$:

$$L_s(x_o,\omega_o) = \frac{\sigma_s(x_o) F}{4\pi} \int_{2\pi} L_i(x_o,\omega_i) d\omega_i,$$

where $\sigma_s$ is the scattering coefficient, and $F = F_t(\eta(x_o),\omega_o) \cdot F_t(\eta(x_o),\omega_i)$, is the product of incoming and outgoing Fresnel transmission terms with $\eta$ being the refractive index. The multiple-scattering component $L_m(x_o,\omega_o)$ consists of light that interacts multiple times within the object volume. For highly scattering, non-emissive materials, multiple scattering may be approximated by a diffusion process described by the following equation $$\nabla \cdot (\kappa(x) \nabla \phi(x)) - \mu(x)\phi(x) = 0, x \in V,$$

with boundary condition defined on the object surface A:

$$\phi(x) + 2C\kappa(x) \frac{\partial \phi(x)}{\partial n} = q(x), x \in A,$$

where:

$$\phi(x) = \int_{4\pi} L_o(x,\omega) d\omega$$

is the radiant fluence (also known as the scalar irradiance), $$\kappa(x) = 1/[3(\mu(x) + \sigma_s'(x))]$$

is the diffusion coefficient, $\mu(x)$ is the absorption coefficient, and $\sigma_s'(x) = \sigma_s(1-g)$ is the reduced scattering coefficient with "g" being the mean cosine of the scattering angle. The exemplary technique can define $C = (1+F_{dr})/(1-F_{dr})$ where $F_{dr}$ is the diffuse Fresnel reflectance. The diffuse incoming light at a surface point x is given by $q(x) =$ $$\int_{\Omega^2} L_i(x,\omega_i)(n\cdot\omega_i) F_t(\eta(x),\omega_i) d\omega_i.$$

With the diffusion approximation, the multiple scattering component of the outgoing radiance is calculated as:

$$L_m(x_o,\omega_o) = -\frac{C}{\pi} F_t(\eta(x_o),\omega_o)\kappa(x_o)\frac{\partial \phi(x_o)}{\partial n},$$

where $\Phi(x_o)$ is computed from the previous equations (diffusion and boundary equations).

As described herein, an exemplary method performs modeling and rendering multiple scattering in a heterogeneous material using the diffusion approximation. For rendering an object with known $\mu(x)$ and $\kappa(x)$ throughout the object volume V, we solve the diffusion problem with a given illumination condition $q(x)$ on the object surface A per the forward problem 320 of FIG. 3. Once the solution $\Phi(x)$ is found, the multiple scattering component of the outgoing radiance can be evaluated using the equation for $L_m$; noting that the diffusion equation assumes scattering to be frequent enough to be considered isotropic and independent of the phase function.

In acquiring the material properties from measured appearance, computation of the absorption coefficients $\mu(x)$ and diffusion coefficients $\kappa(x)$ occurs based on measured outgoing radiances:

$$\{L_{o,m}(x,\omega_o) | x \in A, m=0,1,\ldots M\}$$

from the object surface due to multiple scattering under M different illumination conditions:

$$\{L_{i,m}(x,\omega_i) | x \in A, m=0,1,\ldots M\}$$

on the object surface. For this purpose, an inverse diffusion problem is solved per block 330 of FIG. 3 to find $\kappa(x)$ and $\mu(x)$ such that the corresponding diffusion problem produces the outgoing radiance $L^R_{o,m}(x,\omega_o)$ that is most consistent to the measured outgoing radiance $L_{o,m}(x,\omega_o)$ under the same illumination conditions $L_{i,m}(x,\omega_i)$. The inverse diffusion problem is thus formulated as finding the values of $\kappa(x)$ and $\mu(x)$ throughout the volume that minimize the objective function:

$$\sum_{m=1}^{M} \int_A \int_\Omega (L_{o,m}(x,\omega_o) - L^R_{o,m}(x,\omega_o))^2 dA(x) d\omega_o.$$

To obtain multiple scattering components from image measurements, a cross-polarization may be employed. An exemplary method utilizes an image acquisition scheme described below that minimizes the presence of single scattering and surface reflections in the image data.

As mentioned with respect to the capture block 110 of FIG. 1, to acquire the volumetric material model of a real object, an exemplary method obtains images of the object under different illumination conditions and then solves the inverse problem of light diffusion on the multiple scattering components. In solving the inverse diffusion problem, a search is performed for the volumetric model $(\mu(x), \kappa(x))$ whose forward diffusion solution is most consistent with the acquired images.

In various examples, data capture was performed using a Canon 30D digital camera with a 17-45 mm lens to record images of a material sample that is illuminated by an Optoma DLP projector with a 4500:1 contrast ratio. In these trials, the material samples were all block-shaped and represented as a regular grid with n×m×l sample points (n≧m≧l) on the grid nodes. Depending on sample thickness, two setups were used. In both setups, the sample was positioned so that one of the n×m faces was perpendicular to the optical axis of the projector.

For thin material samples (n,m>>l), the camera was placed facing the sample from the opposite side, such that the sample is imaged with back-lighting. For thick material samples with little transmission of light through the volume, the camera was positioned beside the projector. For sake of explanation, the side of the sample facing the camera is referred to as the front face.

The camera and projector were calibrated prior to image acquisition. Geometric calibration of both the camera and projector was accomplished with a technique where the projector projected a chessboard pattern onto different planes. The white balance of the camera was calibrated with respect to the projector, based on the projection of a white image onto a Macbeth Color Checker™ chart with known albedos. The color chart was also used in measuring the black level of the projector.

To avoid interference effects from the projector's color wheel, exposure times of at least 1/30 second were used. In illuminating the sample, the face that received direct lighting was subdivided into 4×4 regions, and light was separately projected onto each region while capturing an image sequence of the complete sample with a fixed aperture and variable exposure times ranging from 1/30 to 8 seconds. Construction of an HDR image from the image sequence for each illumination condition was performed. Vignetting effects from the projector were minimized by illuminating the sample using only the center of the projector images.

With this capture process, images of multiple scattering data were obtained. In a thin-sample setup, the back-lighting was assumed to scatter multiple times before exiting from the front face, such that captured images contain only multiple scattering. In the setup for thick samples, image data were for only those surface points that were not directly illuminated by the projector, as the appearance of these points is considered to result only from multiple scattering. Since the projector and camera were aligned perpendicularly to the material sample in both configurations, the Fresnel transmittance effects on the measured multiple scattering were disregarded, and the dependence on wo in the inverse diffusion problem equation was dropped. For various examples the following were set: C=2.1489 with h=1.3.

To capture the approximate single scattering term in the equation for $L_s$, the front-lighting setup was used and a technique that records one image of the sample under uniform lighting and the single scattering term was obtained by subtracting the multiple scattering contribution.

In model acquisition per step 120 of the method 100 of FIG. 1, for each captured image and corresponding lighting condition, a data mapping was performed to map onto each grid node on the front and back faces its incoming light intensity and measured outgoing radiance. The material model was then acquired by solving for the scattering parameters ($\kappa$ and $\mu$) of each node in the volume that would result in image appearances most consistent with the measured data. With the M measured images of the material sample, the method aims to minimize the following objective function:

$$f_M(\vec{\kappa}, \vec{\mu}) = \sum_{m=1}^{M} f_m(\vec{\kappa}, \vec{\mu}) + \lambda \sum_{x \in V} \|\nabla \kappa(x)\|^2,$$

where $$f_m(\vec{\kappa}, \vec{\mu}) = \sum_{x \in A} (L_{o,m}(x) - L^R_{o,m}(x))^2$$

measures the consistency between the measured outgoing radiance $L_{o,m}(x)$ from all frontal surface points x and the outgoing radiance $L^R_{o,m}(x)$ that is computed from the estimated scattering parameters with the illumination condition of image m. Note that in $f_m$ the dependence on $\omega_o$ is dropped because of the selected imaging configuration in the trials.

The vectors $\vec{\kappa}$ and $\vec{\mu}$ represent the set of diffusion and absorption coefficients defined over all the grid nodes. Since model acquisition is ill-conditioned with respect to $\kappa$, an exemplary method adds a regularization term:

$$\Sigma_{x \in V} \|\nabla \kappa(x)\|^2$$

to the objective function, where $\lambda$ is set to $1e^{-5}$ in for the trials.

FIG. 4 shows an exemplary technique 400 to minimize $f_M$ that employs a conjugate gradient algorithm. An initialization step 410 initializes the vectors $\vec{\kappa}$ and $\vec{\mu}$ and another initialization step 420 sets an initial search direction. A search loop to minimize the function 430 follows that performs the following: In a compute block 431, compute the gradient of $f_M$ with respect to the vectors over the set of measured images; in a set block 432, set the search direction; in an update block 433 update the search direction (e.g., with the Polak-Ribiere method); in a golden section search block 434 perform a golden section search to find the optimal step size $\lambda'$ along the search direction; and in a solution update block 435, update the material property vectors using the computed gradient and $\lambda'$. The steps 431 to 435 are iterated to update the material property vectors until the objective function falls below a threshold (e.g., set to $\epsilon = 10^{-4} \Sigma_{x \in A} [L_{o,m}(x)]^2$. For trials, this optimization was performed separately on the RGB channels.

To initialize the scattering parameters in the optimization, the volumetric material model was solved under the assumption that it was homogeneous, i.e., all the grid nodes have the same material properties. Since only two unknowns exist in this case, they can be quickly computed using the conjugate gradient procedure with user specified initial values.

A step in conjugate gradient optimization is the computation of the $f_M$ gradient relative to the unknown $\kappa$ and $\mu$ values at each grid node. Since the diffusion equation has no analytic solution, gradients were computed numerically. A straightforward approach for gradient computation is to perturb each of the variables and obtain the resultant change in objective function value. One forward diffusion simulation would then be necessary to compute each gradient. Although this method is feasible for a system with few parameters (e.g., a homogeneous volume), it is impractical for arbitrary heterogeneous volumes which have a large number of unknowns. Specifically, model acquisition for an n×m×l grid with M measurements would require 2×n×m×l×M forward diffusion simulations for each of the iterations, which can be a signification expense.

To significantly expedite gradient computation, an exemplary method uses the adjoint method. To use the adjoint method to provide a solution, first define the adjoint equation of the original diffusion equation as $$\nabla \cdot (\kappa(x) \nabla \phi(x)) - \mu(x) \phi(x) = 0, x \in V,$$

with a boundary condition on the surface A defined as:

$$\varphi(x) + 2C\kappa(x) \frac{\partial \varphi(x)}{\partial n} = \frac{2C}{\pi}(L_{o,m}(x) - L^R_{o,m}(x)), x \in A,$$

where $(L_{o,m}(x) - L^R_{o,m}(x))$ is the difference between the measured outgoing radiance $L_{o,m}(x)$ from all frontal sample points x and the outgoing radiance $L^R_{o,m}(x)$ that is computed from the diffusion equation with the illumination condition $q_m$ of image m. Given $\phi$, the gradient of $f_M$ with respect to $\kappa$ and $\mu$ at each grid point is computed by $$\frac{df_M(\vec{\kappa}, \vec{\mu})}{d\kappa(x)} = \sum_{m=1}^{M} \nabla \varphi_m(x) \cdot \nabla \phi_m(x) - 2\lambda \Delta \kappa(x),$$

$$\frac{df_M(\vec{\kappa}, \vec{\mu})}{d\mu(x)} = \sum_{m=1}^{M} \varphi_m(x) \phi_m(x),$$

where $\Phi_m(x)$ is determined from the diffusion equation with the illumination condition $q_m$ of image m.

In contrast to the original diffusion equation, the adjoint method utilizes "virtual" illumination to define the boundary condition. This virtual illumination $(2C/\pi)(L_{o,m}(x) - L^R_{o,m}(x))$, which may be negative, and $\Phi$ are computed from the diffusion equation using the actual illumination condition. With the virtual illumination, an exemplary method solves the adjoint equation for $\phi$, and then determines the gradient of $f_M$ relative to $\kappa$ and $\mu$ using the foregoing equations. Using the adjoint method, only 2M forward diffusion simulations are needed for gradient computation.

Various exemplary methods described herein may be implemented using one or more graphics processing units (GPUs). A GPU is typically used for computing 3D functions such as lighting effects, object transformations and 3D motion.

Referring to the model acquisition step 120 of the method 100 of FIG. 1 and the forward problem 320 of FIG. 3, forward diffusion simulations can be used not only in gradient computation, but also for evaluating the objective function in the golden section search, which is presented as step 434 of the technique 400 of FIG. 4. An exemplary approach to solving the diffusion equation on a 3D regular grid includes discretizing the diffusion equation over the grid nodes and numerically solving the resulting system of equations using a multigrid finite difference method (FDM) scheme.

Such a FDM technique involves considerable computation and can be the bottleneck in model acquisition. As described herein, for efficient processing, an exemplary GPU-based multi-resolution scheme that simulates forward diffusion in the pixel shader on grid values of $\kappa$, $\mu$, and q packed into separate 2D textures. This GPU-based scheme can be regarded as a regular-grid version of the rendering algorithm discussed further below.

In solving the diffusion equation on a GPU configured for 3D computations, relevant data is uploaded from main memory to texture memory, and then the radiant fluence results are output from a frame buffer back to main memory. The remaining optimization computations are all executed on a general CPU. Despite some overhead for data transfer, an appreciable overall reduction in computation costs is obtained through GPU acceleration.

In theory, the diffuse bidirectional surface scattering reflection distribution function (BSSRDF) should be densely sampled to ensure that the acquired material volume generates accurate surface appearances for arbitrary illumination conditions. However, because of the redundancy in BSSRDF data, various trials demonstrate that models acquired from sparsely sampled images provide acceptable results in practice; noting that each image here corresponds to a 2D slice of a 4D BSSRDF.

To examine the relationship between the number of measurements and model quality, an exemplary model acquisition algorithm was applied on a synthetic volume, which was modeled using a 72×72×10 grid. The front surface was divided into n×n regions that were each separately illuminated. For different n, images were generated using the diffusion equation, and then these images were used as input to the algorithm. Normalized errors were then computed as:

$$E = \Sigma x_i, x_j \in A [R_d'(x_i, x_j) - R_d(x_i, x_j)]^2 / \Sigma x_i, x_j \in A [R_d(x_i, x_j)]^2$$

where $R_d$ is the diffuse BSSRDF computed from the original volume, and $R'_d$ is that computed from the acquired material volume. The trials were performed with both front-lighting and back-lighting setups. In an error analysis, for n=1, 2 . . . 8, the analysis indicated that for 16 or more images, the error is comparable to that reported for the factorized BSSRDF representation in a prior study. In various trials, 16 images were used under different illumination settings for model acquisition, which provided an acceptable level of rendering quality.

As explained with respect to the steps 110 and 120 of FIG. 1, after acquiring a material model from a real sample of a material (which may be a composite material), per the step 130 of FIG. 1, a virtual volume of arbitrary shape can be formed with this material using material mapping techniques. A mapping approach map the material properties into a shell layer at the object surface, and construct the inner core volume by synthesizing a user-specified material texture or interpolating from the inner boundary of the shell layer using mean value coordinates.

Figure 5:
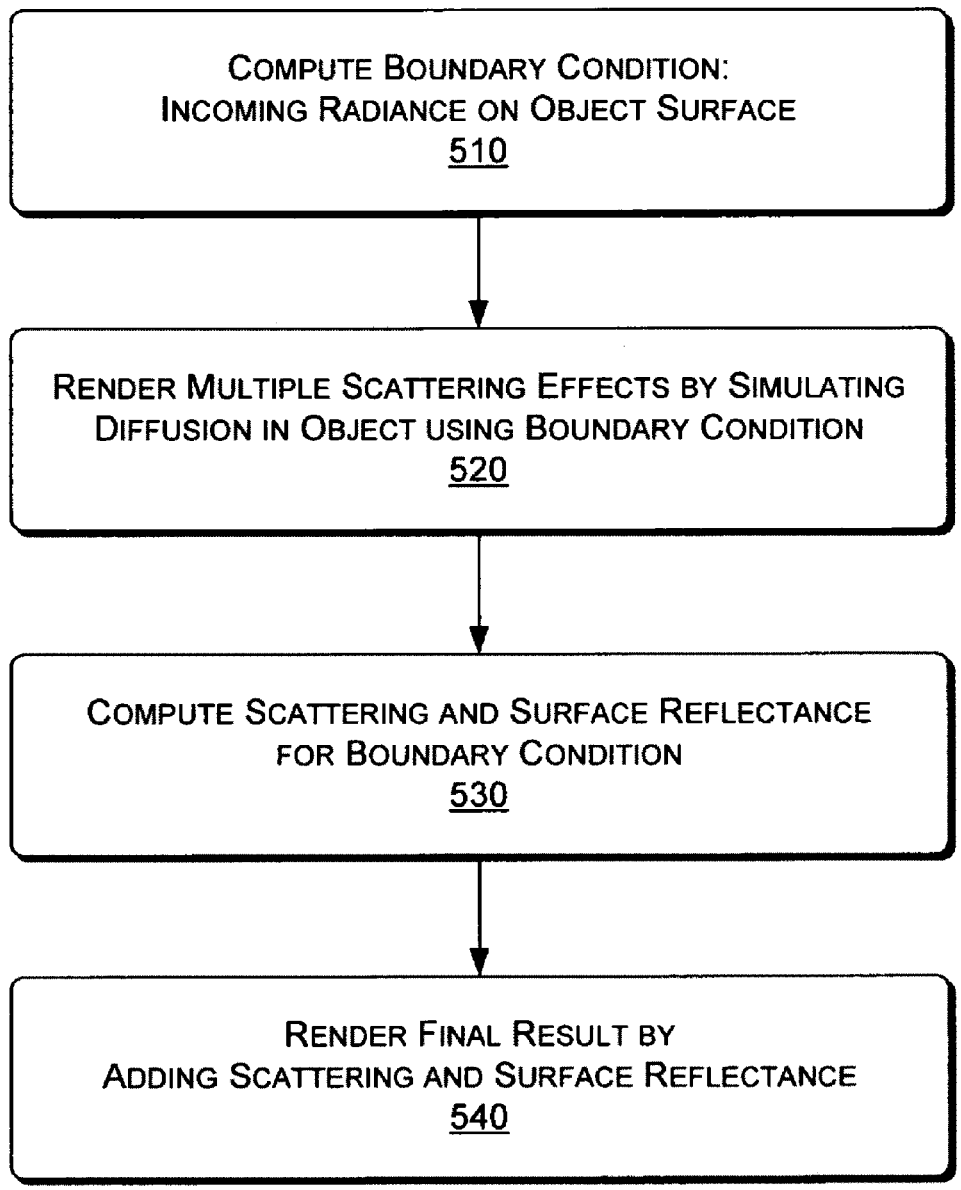
FIG. 5 is a diagram of an exemplary method for rendering a virtual object using a diffusion equation approach.

FIG. 5 shows an exemplary method 500 for rendering a final result that includes scattering and surface reflectance. As described herein, with a given lighting condition and material properties defined throughout some object volume (which may be part of a larger volume), subsurface scattering effects from the object volume can be rendered.

In a computation block 510, computation of the incoming radiance on the object surface occurs (e.g., based on shadow map visibility for directional or point lighting or from pre-computed radiance transfer techniques for environment lighting). As already explained, a 3D diffusion equation (a partial differential equation for a 3D space) is used to describe "light" diffusion phenomenon in a volume given an appropriate boundary condition. In the method 500 of FIG. 5, the boundary condition, on the surface of the object volume, is computed as the incoming radiance.

In a rendering block 520, rendering of multiple scattering effects occurs by simulating light diffusion inside the object volume with the incident radiance on the surface as the boundary condition. In another computation block 530, computation of the single scattering term and surface reflectance from the incoming illumination occurs. To render the final result, another rendering block 540 obtains the final rendering result by adding the scattering and surface reflectance components.

To efficiently solve for light diffusion using a GPU, the aforementioned FDM scheme is extended on regular volumetric grids to handle a polygrid defined in (or as) the object volume. An exemplary polygrid is a grid with regular 6-connections among evenly distributed nodes inside the volume, and that has boundary nodes that are aligned with the object surface and where each is connected to one interior node along the inward normal direction. With the polygrid representation of an object volume, it is possible to discretize the light diffusion equation and its boundary condition into a system of linear equations:

$$\sum_{j=1}^{6} w_{ji} \kappa(v_j) \phi(v_j) - \left( \sum_{j=1}^{6} w_{ji} \right) \kappa(v_i) \phi(v_i) - u(v_i) \phi(v_i) = 0,$$

-continued $$\phi(v'_i) + 2C\kappa(v'_i)\frac{\phi(v'_i) - \phi(v'_j)}{d_{ji}} = q(v'_i)$$

where $v_j$ denotes one of six nodes directly connected to interior node $v_i$ with a weight $w_{ji}$ for the Laplacian operator. The parameter $d_{ji}$ represents the distance between a boundary node $v'_i$ and the closest interior node $v'_j$ along the inward normal direction, and $q(v'_i)$ denotes the incoming radiance at surface node $v'_i$.

Discussed below are techniques to construct a polygrid of an object volume and to solve the diffusion equation (e.g., using a GPU). An exemplary hierarchical scheme is also presented for accelerating GPU evaluation of light diffusion on a polygrid.

FIG. 6 shows an exemplary technique 600 to construct a polygrid for an object. In a creation step 604, a ploycube is assembled of similar topology that approximates the volume. This step may be automated or occur manually. In FIG. 6, the polycube includes individual cubes grouped together to represent the volume.

In a generating step 608, within each of the cubes, regular grids of equal resolution are formed and the grids are connected between adjacent cubes. As indicated in FIG. 6, the grid includes boundary nodes and interior nodes. Interior nodes are directly linked to boundary nodes on the edges or corners of a cube and have connectivity to multiple boundary nodes, which may lead to artifacts in the light diffusion computation. To address this artifact problem, a modifying step 612 modifies certain nodes and links. As shown, certain nodes are removed and links adjusted to obtain single connections to boundary nodes.

With respect to corners, FIG. 6 shows a corner scheme 640 and a corner scheme 650. These schemes were used to examine axis-aligned 2D slices of the grid. An exemplary method for a polygrid can utilize one or more different grid adjustment schemes, for example, depending on the grid convexity in a slice. By applying the schemes 640 and 650, one arrives at a polygrid defined in the polycube.

To proceed, a projecting step 616 determines a projection of the polycube surface onto the object surface using a PolyCubeMap or other mesh cross-parameterization method. A mapping step 620 relies on the projecting to maps the polygrid to the object volume. The mapping step 620 maps the boundary nodes of the polygrid to the object surface, which may be adjusted to obtain an even distribution.

After the mapping step 620, a computing step 624 acts such that the interior nodes directly connected to the boundary nodes are placed within the object volume at a distance "d" along the inward normal directions, where "d" is appropriately set (e.g., one-tenth the average distance between connected boundary nodes on the object surface). Close placement of these nodes to the boundary nodes is intended for accurate handling of the boundary condition. In other words, the boundary condition determines the volumetric solution; hence, the polygrid should be appropriately spaced at the interior adjacent the boundary of the object to accurately account for the effect of the boundary condition on the entire volumetric solution. Further, gradients can often be the largest at the boundary. For other interior nodes (i.e., the remaining interior nodes), these are then positioned within the volume in an appropriate manner. In the example of FIG. 6, the manner for positioning the remaining interior nodes minimizes the variance of distances between connected nodes:

$$\min \Sigma_{i \in interior} \text{Var}(\{\|v_i - v_j\|: j \bowtie i\})$$

where Var(−) denotes the variance of a set of scalars, $v_i$ is the 3D position of node i, and $j \bowtie i$ indicates that node j is connected to node i. In principle, a conformal mapping can be used to preserve the orthogonality of the original grid connections and minimize distortion. However, various trials demonstrate that the aforementioned variance minimization scheme yields acceptable solutions.

The technique 600 of FIG. 6 maintains regular connectivity of nodes and produces locally uniform distributions of interior grid nodes in the object volume. When applied to a volume, the interior grid nodes of a polygrid are 6-connected, and each boundary node is connected to exactly one interior node. In various trials, connectivity between the boundary grid nodes is not used in rendering and can be ignored in the diffusion computation.

As mentioned, with the constructed polygrid, a system of linear equations for light diffusion can be generated. The material properties for each grid node are sampled from the object volume, and the incoming illumination is computed for boundary nodes. Although a general purpose GPU-based linear system solver could be used for computation, various trials include use of an exemplary GPU-based that is efficient GPU and specific to diffusion computation on a polygrid.

In this exemplary method, the polygrid material parameters are packed into a set of 2D textures for computation on a GPU. For efficient rendering, the textures are packed such that the connected neighbors of each node are easily accessible. Towards this end, each texture is organized according to the positions of the polygrid nodes within the original polycube. The cubes in the polycube are transferred in scanline order, and the grid of each cube is flattened. The grid in each cube is divided into 2D x-y slices, which are each treated as a texture block and ordered in the texture by increasing z value. In packing the texture, empty positions of grid nodes are retained that were previously removed, so that the cubes have slices of equal size. Two 2D textures $T_\kappa$ and $T_\mu$ are created for the corresponding scattering parameters, and for the iterative computation two swap radiance buffers IA and IB are maintained that are organized in the same manner as $T_\kappa$ and $T_\mu$. In addition, precompute of the weights for the Laplacian operator occurs, then this data is similarly packed into two textures $T_{w1}$ and $T_{w2}$. The incoming radiance is also packed into a 2D texture $T_I$ according to access order as described further below.

After texture packing, the diffusion equations are solved on the polygrid using a relaxation scheme. Starting from the initial radiant fluence values $f_0$, the scheme iteratively update the radiant fluence values in the two radiance buffers until convergence. With the radiant fluence at each node corresponding to one pixel in the radiance buffer, this computation can be executed in the pixel shader with parameters accessed from the textures. To reduce texture fetches in the pixel shader, $f' = K_f$ is stored in the radiance buffer. In each step, the radiant fluence values are updated as follows:

$$\phi'_{n+1}(v_i) = \frac{\sum_{1 \le j \le 6} w_{ji}(v_i)\phi'_n(v_j)}{\mu(v_i)/\kappa(v_i) + \sum_{1 \le j \le 6} w_{ji}(v_i)},$$

$$\phi'_{n+1}(v'_i) = \frac{q(v'_i)\kappa(v'_i)\kappa(v'_j)d + 2C\kappa^2(v'_i)\phi'_n(v'_j)}{\kappa(v'_j)d + 2C\kappa(v'_i)\kappa(v'_j)},$$

where right-hand-side operators of the form f (·) involve a texture access, and the radiance buffer for $f'_n$ is used as the texture while the other radiance buffer is used as rendering target for $f'_{n+1}$.

In the foregoing exemplary scheme, there exist three types of nodes/pixels in the radiance buffer, each with different texture access patterns for reaching connected nodes. These nodes/pixels are referred to as type A, type B and type C. Each type of node is rendered using a different geometric primitive. For a node that lies in the interior of a texture block (type A node), four of its connected neighbors in the polygrid are also adjacent neighbors in the 2D texture, while the other two neighbors can be found with the same offset value in other texture blocks. The values of these nodes are updated by rendering a quadrilateral with the texture offsets of the two non-adjacent neighbors as vertex attributes. After rasterization, this offset information can be interpolated from the vertices to each pixel in the quad. In a similar manner, nodes on each texture block edge (type B nodes) are rendered with a line, where three neighbors are adjacent in the texture, and the texture offsets of the other three are stored as line vertex attributes. The nodes of each texture block corner (type C nodes) are rendered with points, with the texture offsets of all six neighbors stored as vertex attributes.

Slices that contain removed nodes can also be rendered using these three primitives (types A, B and C). All of these geometric primitives and their vertex attributes can be precomputed and loaded into graphics memory before rendering. Since the surface boundary nodes and the interior nodes are processed differently, their corresponding geometric primitives can be rendered in two separate passes with different pixel shaders. After completing such a computation, the output radiance can be calculated on the surface by updating the boundary nodes in the radiance buffer as:

$$L(v'_i) = F_t(x_o, w_o)[\phi'(v_i) - q(v_i)\kappa(v_i)]/[2\pi\kappa(v_i)]$$

These boundary node values are then used as a texture for surface vertices in the final pass.

With the foregoing exemplary packing and rendering scheme, the radiant fluence values are updated with 10 texture fetches for interior nodes and 5 texture fetches for surface nodes. Such a scheme avoids extra texture storage for node connectivity information and dependent texture accesses in rendering. Alternative schemes for packing and rendering are possible; nevertheless, the foregoing exemplary scheme obtains good performance.

For greater efficiency in computing light diffusion, an exemplary hierarchical scheme is employed to accelerate rendering with a polygrid. In this hierarchical scheme, a multi-resolution polygrid in the object volume is constructed. Starting from the original polygrid, the positions and material properties of nodes at successively coarser levels are determined by averaging the positions and material properties of its eight children at the next finer level. For nodes whose children contain removed nodes, the result is normalize by the number of existing children. Before rendering, the material properties at each resolution are packed and texture pyramids generated for $T_\kappa$, $T_\mu$, $T_{w1}$ and $T_{w2}$.

Pyramids need not be generated for the radiance buffers IA and IB, which can simply be reused for computation at each level. During rendering, a process first solves the diffusion equations at the coarsest grid level, and then uses the computed radiant fluence at each node as initializations for its children nodes at the next finer level. This process iterates until a solution at the original polygrid resolution is obtained.

The hierarchical algorithm can be accelerated by employing an adaptive scheme in which light diffusion is computed at different resolutions at different depths in the volume. Since material variations deeper inside the object volume have more subtle effects on surface appearance, it is sufficient to approximate light diffusion at deeper nodes with coarser-resolution solutions.

According to such a coarser-resolution approach to deeper nodes, after obtaining the solution at a coarse resolution and copying it to a finer resolution, the radiant fluence values at nodes below a certain depth are fixed, while the nodes closer to boundary are updated. In such an implementation of this adaptive scheme, the computed resolution at different depth levels can be given by a user. Texture blocks whose nodes are not used in computation at a given level can be removed to save on texture storage.

Various examples are implemented without using the V-cycle multigrid algorithm to speed up light diffusion computation, as a cost exists for incorporating the multigrid algorithm into the foregoing adaptive scheme. Also, V-cycle multi-grid algorithms require extra texture storage for residual and temporary radiant fluence values in each level. If all grid nodes are used in light diffusion, the foregoing exemplary technique may be considered as a simplified N-cycle multigrid scheme without V-cycles for each resolution.

A favorable property of the light diffusion algorithm is that the coherence between frames can be exploited to facilitate rendering. For applications in which the lighting or material changes gradually, the rendering result of the last frame provides an excellent initialization for the current frame. With good initial values, the number of iteration steps can be significantly reduced.

An exemplary hierarchical method for rendering a virtual object volume includes constructing a multiresolution polygrid in the virtual object volume; generating texture pyramids for material properties of the virtual object volume; and rendering the virtual object volume by solving diffusion equations at a coarse grid level and computing radiant fluence at a finer grid level. Such a method my include accelerating the rendering using an adaptive scheme that computes light diffusion at different resolutions at different depths in the virtual object volume.

An exemplary real-time rendering system allows for an acquired volumetric material model to be interactively edited with real-time feedback on the modified appearance. In a trial that illustrates this capability, the exemplary GUI 200 of FIG. 2 was used. In addition to painting new values for $\mu(x)$ and $\kappa(x)$, various ways to modify existing $\mu(x)$ and $\kappa(x)$ can be supported. The user can directly adjust $\mu(x)$ and $\kappa(x)$ by multiplying them with or adding them to user-supplied constants (strength control of the field 212). Alternatively, the user can modulate the $\mu$ and $\kappa$ values within a pattern mask using a texture (the paint/fill field 220 and the stamp pattern field 224). With volumetric representation, users can also modify a material at specific depth levels (depth control of the field 212).

In an exemplary system, all editing operations can be executed as pixel operations on a GPU. Such a system can maintain extra buffers $T'_\kappa$ and $T'_\mu$ of the $\kappa$ and $\mu$ textures as rendering targets for editing. In each frame, $T'_\kappa$ and $T'_\mu$ can be modified by user-specified operations, and then swapped to $T_\kappa$ and $T_\mu$ for rendering. To support editing operations on local regions, positions of grid nodes can be stored in a texture $T_p$. Then when a user selects a region on the screen for editing, computation of the screen projection of each grid node based on its position in the editing shader can occur and execution of the editing operations only for the nodes within the user-specified local region can occur.

In the foregoing example of material editing, the adaptive scheme is not implemented; instead, the illustrative trial takes advantage of the coherence between frames to reduce rendering computation, which allows for more complex material editing operations to be executed on a GPU.

As mentioned, various trials were performed to illustrate various exemplary techniques and their results. An exemplary trial implemented material acquisition and rendering system on a PC configured with an INTEL® Core2Duo 2.13 GHZ CPU, 4 GB memory, and a NVIDIA® Geforce 8800GTX graphics card with 768 MB graphics memory. The exemplary GPU-based light diffusion and rendering algorithm was implemented in the OpenGL shading language. For the GPU-based light diffusion computation used in model acquisition, all parameters and computation results were represented as 32-bit floating-point values for high precision. For light diffusion computations on the polygrid, each channel of κ and μ was quantized into 8-bits and stored together in 24-bit textures. The trials used 16-bit floatingpoint values in rendering computations, which provided sufficient precision in appearance.

For various samples, the grid resolutions, lighting configurations, and computation times are listed in Table 1, below. With GPU acceleration, the reconstruction algorithm gains a fifty-fold increase in speed over a CPU-based implementation on the same platform.

TABLE 1

Acquisition settings for different materials.

| Material Grid | Resolution | Illumination | Computation Time |
| --- | --- | --- | --- |
| Wax I | 130 × 53 × 37 | back | 2.0 h |
| Wax II | 140 × 75 × 48 | front | 4.0 h |
| Marble | 256 × 256 × 20 | back | 11.0 h |
| Artificial Stone | 128 × 128 × 41 | back | 3.0 h |

Table 2, below, lists the polygrid resolution at the finest level, the texture size, and rendering performance for various trial examples. In Table 2, for the rendering times, $t_i$ indicates the time for the ith rendering pass. The final speed is measured both without frame coherence and with frame coherence (in parentheses).

TABLE 2

Rendering configuration and performance.

| Model | Polygrid Resolution | Texture Size (MB) | Rendering Time (ms) $t_1/t_2/t_3$ | Final Speed (fps) |
| --- | --- | --- | --- | --- |
| Bunny | 253 × 16 × 16 × 16 | 24.9 | 3.9/23.2/11.5 | 25.9 (34.7) |
| Bust | 17 × 32 × 32 × 32 | 18.9 | 2.5/19.9/7.0 | 34.0 (52.7) |
| Bird | 108 × 24 × 24 × 24 | 39.6 | 4.0/48.3/1 3.0 | 15.3 (24.0) |
| Hole | 36 × 12 × 12 × 12 | 4.8 | 1.5/8.9/2.1 | 80.0 (160.4) |
| Snail | 81 × 12 × 12 × 12 | 18.9 | 1.6/14.0/3.1 | 53.4 (106.7) |

The polygrid resolution is the product of the number of cubes in the polycube and the grid resolution in each cube. The texture size includes all textures used for light diffusion computation. In Table 2, the rendering times are broken down into the three passes, for incident light computation ($t_1$) (e.g., the step 510 of the method 500), light diffusion ($t_2$) (e.g., the step 520 of the method 500), and final rendering ($t_3$) (e.g., steps 530 and 540 of the method 500).

For the overall rendering speed, the first number reports the frame rate without frame coherence (i.e., radiances initialized to zero), while the second number in parentheses gives the speed with frame coherence. In rendering, ambient occlusion was used to determine visibility for environment lighting and the shadow buffer was used for visibility of local lighting. A three-level polygrid with the adaptive scheme is used in the measurements for Table 2.

With respect to convergence speed of the different rendering methods, the error of a result L is computed as:

$$\Sigma_{x \in A}(L(x)-L_0(x))^2 / \Sigma_{x \in A} L_0(x)^2$$

where $L_0$ is the converged result precomputed without hierarchical and adaptive acceleration. A multi-resolution polygrid with three levels was used in trial hierarchical schemes. The polycube for the aforementioned hole model of Table 1 included 36 cubes where the grid resolution in each cube at the finest level was 12×12×12. For the hierarchical method without the adaptive scheme, all grid nodes were used in the light diffusion computation. In the adaptive scheme, the depth of nodes that were involved in computing each resolution were manually specified such that the final error was less than 0.5%. Results indicate that the hierarchical scheme can substantially improve light diffusion performance on a polygrid. Specifically, hierarchical and adaptive schemes had error less than 0.5% after processing of about 90,000,000 nodes or less; whereas, for a single resolution scheme, error approached 0.5% only after about 450,000,000 nodes. More specifically, with the adaptive scheme, the computation is further accelerated (a two-fold speedup in this case) to generate a result with an error below a user-specified threshold.

Figure 7:
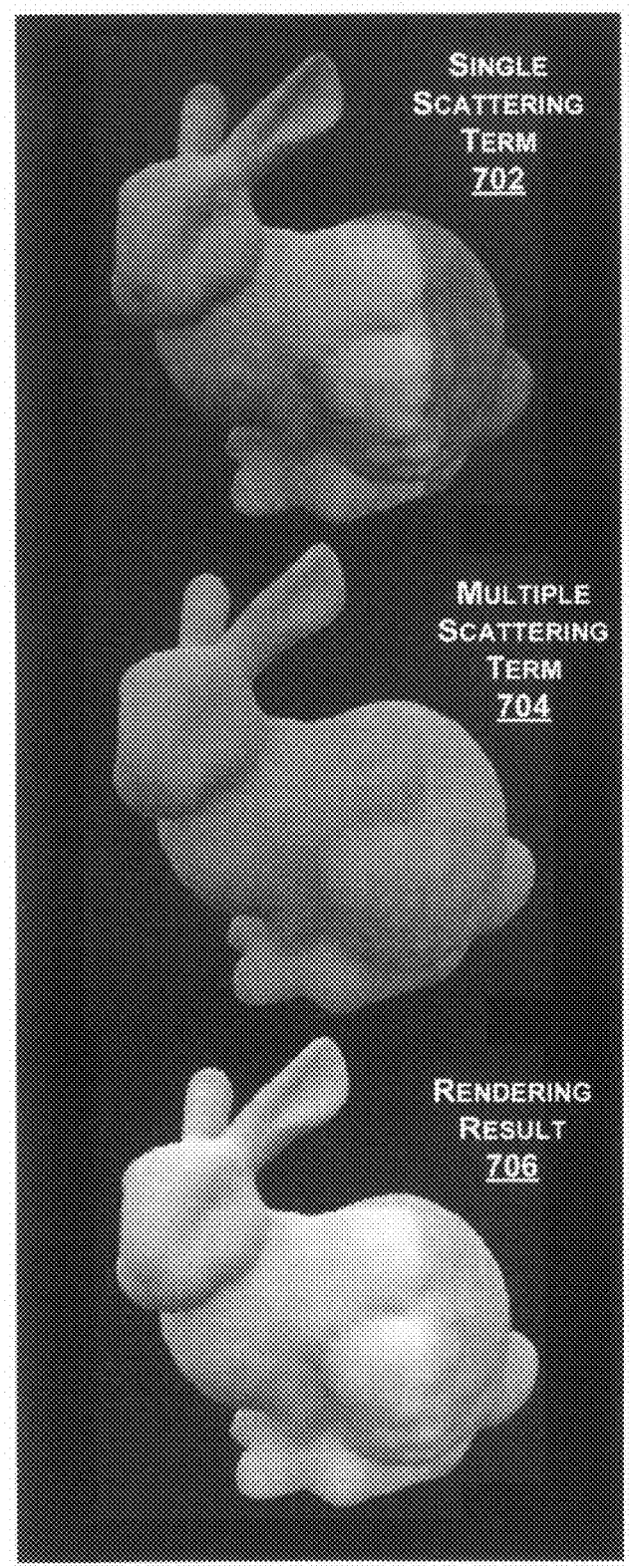
FIG. 7 is a series of visual renderings for a virtual object where scattering terms are used to produce a final result.
Figure 8:
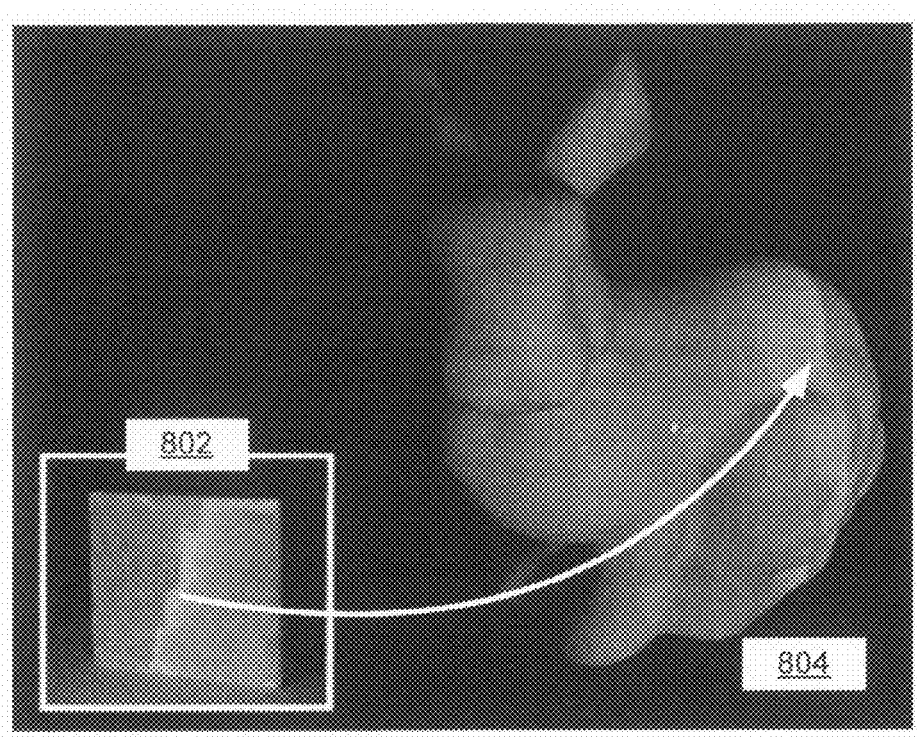
FIG. 8 is a photograph of a sample material and a visual rendering of a virtual object having material properties of the sample.

FIG. 7 shows different scattering components including a single scattering term 702 and a multiple scattering term 704 along with an overall rendering result 706 for a bunny model under environment lighting. The overall result is the sum of the two components 702 and 704. FIG. 8 shows a photograph of the original sample material 802 along with a rendering of the bunny model 804 that corresponds to the bunny of FIG. 7.

In a bust model, whose volumetric material properties were acquired from a marble sample, and a hole model (e.g., an object with a hole), generated with acquired wax material, complex surface appearances from subsurface scattering and volumetric material variations were well preserved using exemplary techniques for volumetric appearance modeling.

Figure 9:
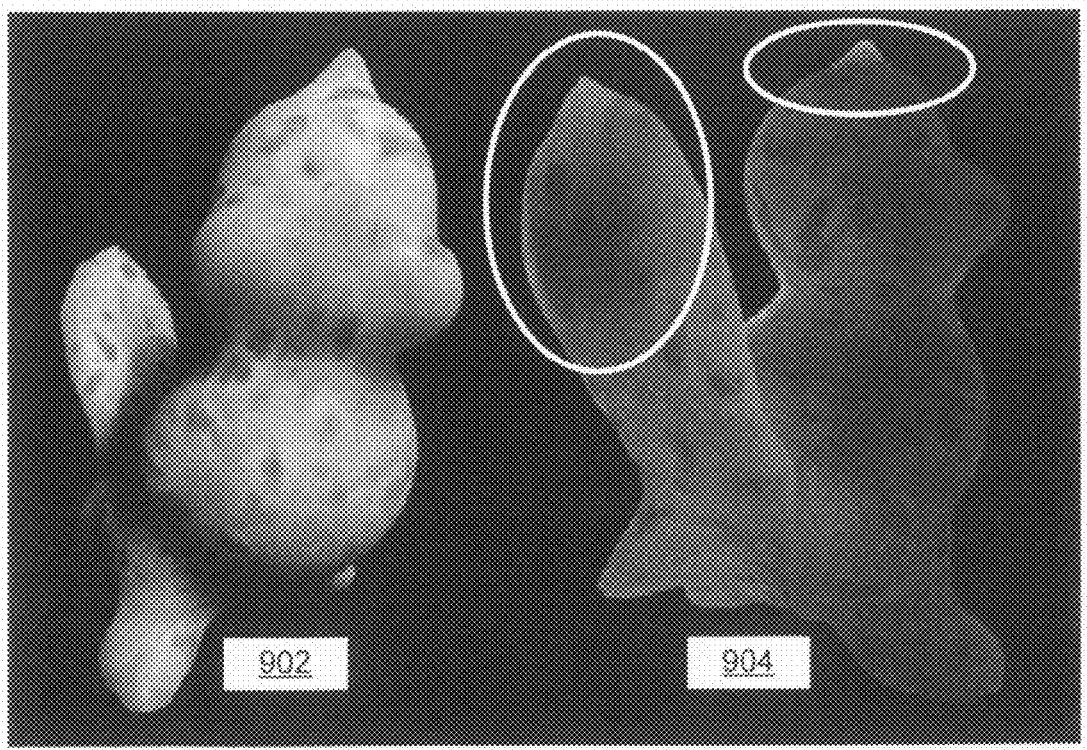
FIG. 9 is a visual rendering of a virtual object.

In FIG. 9, a bird model is rendered with an artificial stone material. Results are shown from different viewing directions 902 and 904. The heterogeneity beneath the surface is well handled in the modeling and rendering technique. In the view 904, white ovals indicate portions of the model where thickness plays a role in translucency. At both the end of the bird tail and top of the bird head, the thinner portions of the bird allow more light to pass through.

In various other trials, local scattering properties of the material and their distributions were modified. With the volumetric material model, editing of physical attributes can be done in an intuitive manner (see, e.g., the GUI 200 of FIG. 2)

Figure 10:
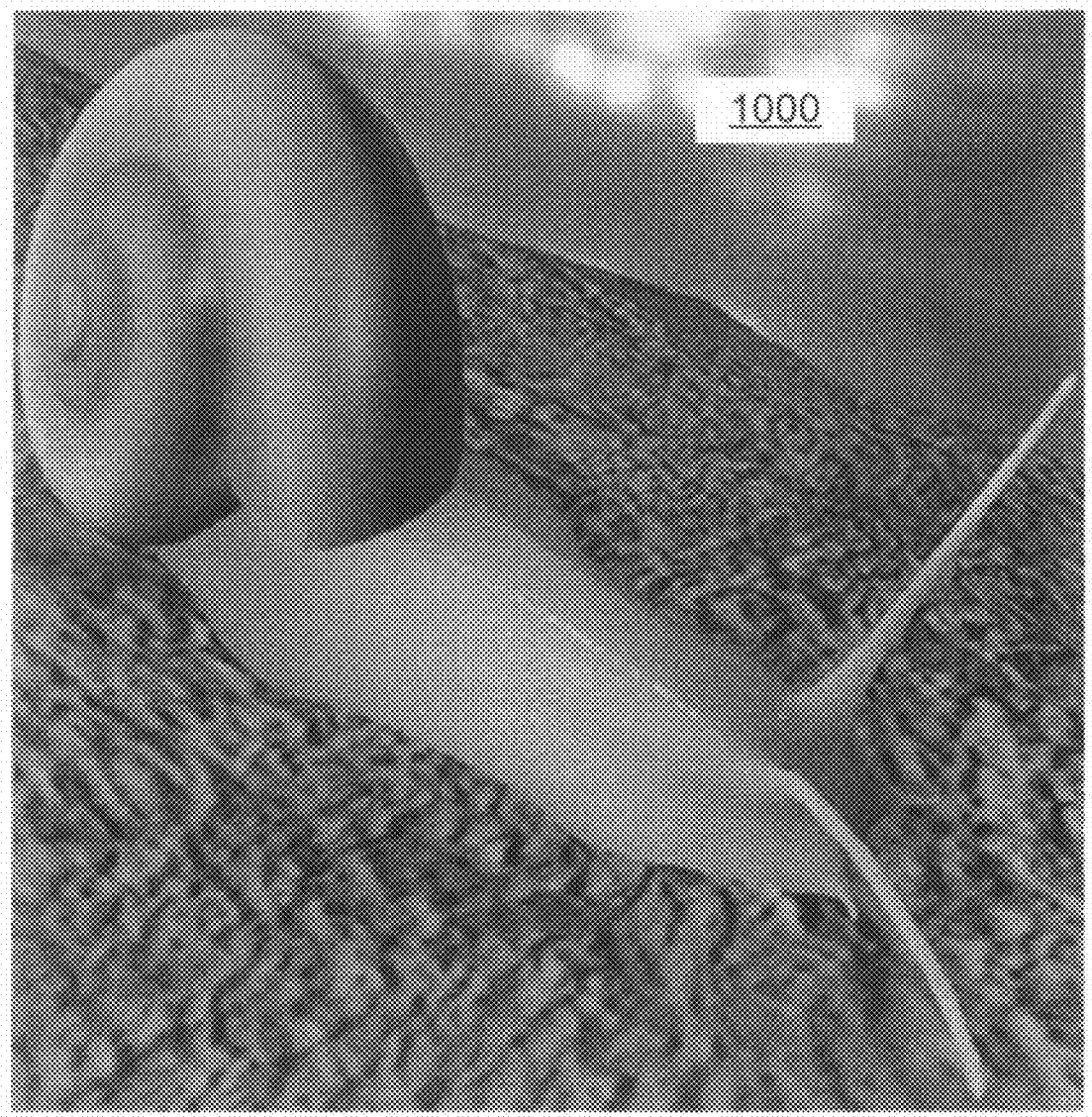
FIG. 10 is a visual rendering of a virtual object that included editing using the GUI of FIG. 2.

FIG. 10 shows a result 1000 from another trial where a snail model was rendered. In this model, the volumetric material properties of the snail body were designed by an artist using the GUI 200 editing tool. The artist also painted the surface texture and opaque snail shell.

Described herein are various exemplary techniques for diffusion equation modeling and rendering of heterogeneous translucent materials. An exemplary scheme is presented for acquiring volumetric appearance models from real material samples, and for rendering the appearance effects of multiple scattering in real time. With such a scheme, a user can easily edit translucent materials and their volumetric variations with real-time feedback. Images show how such an approach effectively acquires a detailed appearance model of subsurface scattering.

In rendering, an exemplary polygrid representation leads to an approximate FDM solution for arbitrary-shaped object volumes. With this approximation, realistic rendering results can be obtained and with real-time performance.

Figure 11:
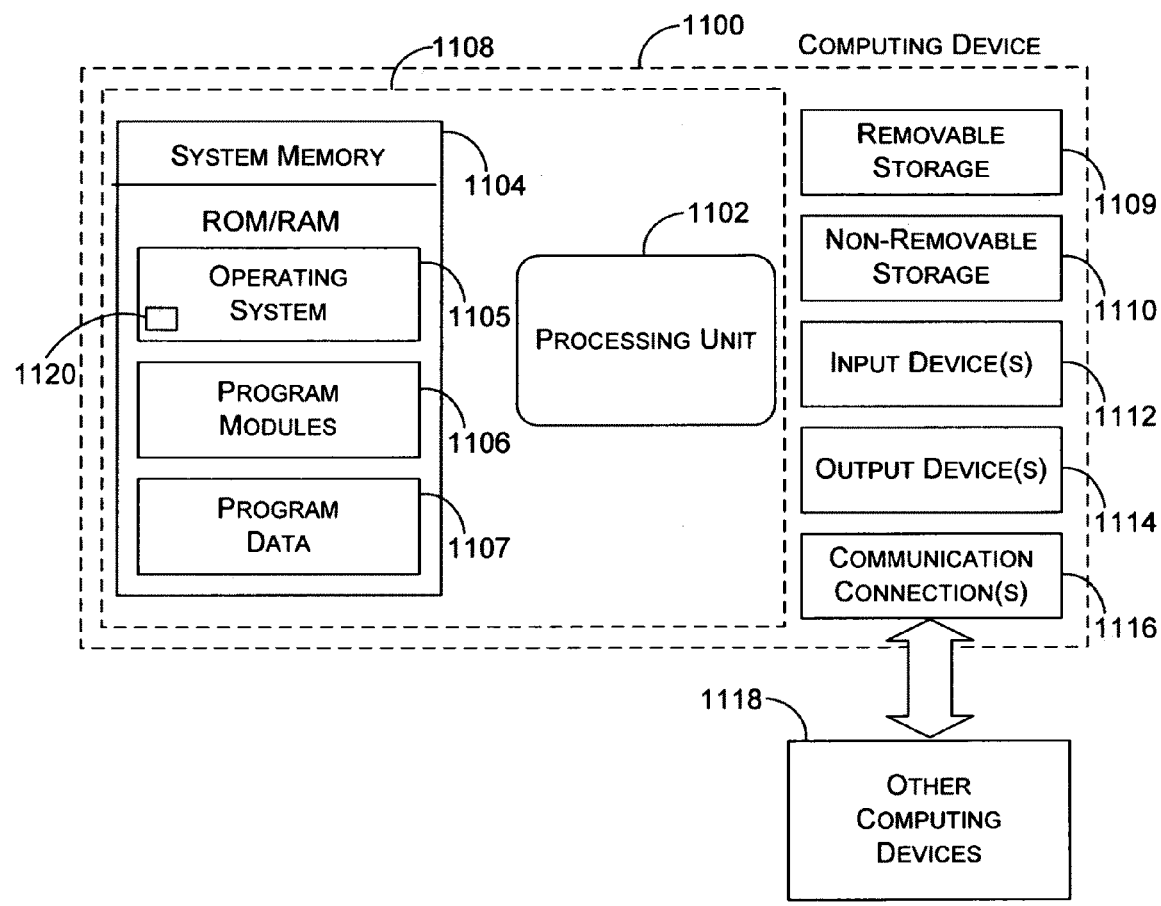
FIG. 11 is a block diagram of an exemplary computing device.

FIG. 11 illustrates an exemplary computing device 1100 that may be used to implement various exemplary methods and in forming an exemplary system. In a very basic configuration, computing device 1100 typically includes at least one processing unit 1102 and system memory 1104. Such a computing device 1100, as mentioned, may include one or more GPUs (not shown). Depending on the exact configuration and type of computing device, system memory 1104 may be volatile (such as RAM), non-volatile (such as ROM, flash memory, etc.) or some combination of the two. Memory may be configured as described above for an exemplary implementation that includes a GPU.

System memory 1104 typically includes an operating system 1105, one or more program modules 1106, and may include program data 1107. The operating system 1105 include a component-based framework 1120 that supports components (including properties and events), objects, inheritance, polymorphism, reflection, and provides an object-oriented component-based application programming interface (API), such as that of the .NET™ Framework manufactured by Microsoft Corporation, Redmond, Wash. The device 1100 is of a very basic configuration demarcated by a dashed line 1108. Again, a terminal may have fewer components but will interact with a computing device that may have such a basic configuration.

Computing device 1100 may have additional features or functionality. For example, computing device 1100 may also include additional data storage devices (removable and/or non-removable) such as, for example, magnetic disks, optical disks, or tape. Such additional storage is illustrated in FIG. 11 by removable storage 1109 and non-removable storage 1110. Computer storage media may include volatile and nonvolatile, removable and non-removable media implemented in any method or technology for storage of information, such as computer readable instructions, data structures, program modules, or other data. System memory 1104, removable storage 1109 and non-removable storage 1110 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 1100. Any such computer storage media may be part of device 1100. Computing device 1100 may also have input device(s) 1112 such as keyboard, mouse, pen, voice input device, touch input device, etc. Output device(s) 1114 such as a display, speakers, printer, etc. may also be included. These devices are well know in the art and need not be discussed at length here.

Computing device 1100 may also contain communication connections 1116 that allow the device to communicate with other computing devices 1118, such as over a network. Communication connections 1116 are one example of communication media. Communication media may typically be embodied by computer readable instructions, data structures, program modules, or other data forms. By way of example, and not limitation, communication media includes wired media such as a wired network or direct-wired connection, and wireless media such as acoustic, RF, infrared and other wireless media. The term computer readable media as used herein includes both storage media and communication media.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method comprising:
providing image data for an illuminated physical sample of a heterogeneous translucent material; and
determining, by a computing device, one or more material properties of the material based in part on a diffusion equation wherein one of the material properties comprises a diffusion coefficient for diffusion of radiation in the material, the determining comprises:
including a regularization term for the diffusion coefficient; and
solving an inverse diffusion problem for the one or more material properties, the inverse diffusion problem comprising a distribution of spatially variant absorption and diffusion coefficients;
wherein the solving comprises:
computing a gradient of an objective function associated with the inverse diffusion problem;
setting a search direction along the gradient;
setting a step size; and
computing the gradient of the objective function based on the search direction and the step size.

2. The method of claim 1, wherein the image data comprises measured outgoing radiances from the illuminated physical sample.

3. The method of claim 1, wherein the image data corresponds to known illumination conditions.

4. The method of claim 1, wherein the solving an inverse diffusion problem for the one or more material properties is based in part on measured outgoing radiances and known illumination conditions.

5. The method of claim 1, wherein the determining comprises a graphics processing unit (GPU)-based technique that comprises simulating forward diffusion using a pixel shader for a virtual object volume that represents the physical sample.

6. The method of claim 1, wherein the determining comprises computing gradients for the one or more material properties using a conjugate gradient based algorithm.

7. The method of claim 6, wherein the determining further comprises a golden section search.

8. The method of claim 1, wherein the determining comprises computing gradients for the one or more material properties using an adjoint method.

9. The method of claim 1, further comprising:
mapping the one or more material properties to a virtual object volume;
assigning virtual illumination conditions to the virtual object volume; and
rendering the virtual object volume using the virtual illumination conditions as a boundary condition for a system of diffusion equations of the virtual object volume.

10. The method of claim 1, wherein the setting a step size comprises performing a golden section search to set the step size.

11. Computer-readable storage media with computer-executable instructions stored thereon, the instructions directing a processing unit to perform acts comprising:

determining a volumetric material model of a heterogeneous translucent material, the volumetric material model including an absorption coefficient for absorption of radiation in the material and diffusion coefficients for diffusion of radiation in the material, the determining comprising:

incorporating a regularization term to the diffusion coefficient; and solving an inverse diffusion problem for one or more material properties of the volumetric material model, the inverse diffusion problem comprising a distribution of spatially variant absorption and diffusion coefficients, the solving based on measured outgoing radiances of the heterogeneous translucent material from a known illumination condition;

wherein the solving further comprises:

computing the gradient of an objective function associated with the inverse diffusion problem, setting a search direction along the gradient, setting a step size, and computing the gradient of the objective function based on the search direction and the step size.

12. The computer-readable storage media of claim 11, wherein the measured outgoing radiances are included in image data.

13. The computer-readable storage media of claim 11, wherein the known illumination condition corresponds to image data.

14. The computer-readable storage media of claim 11, wherein the solving further comprises:

setting initial properties of the volumetric material model;
setting a search direction to an initial search direction;
iterating steps until an objective function associated with the inverse diffusion problem meets a desired accuracy threshold, the steps comprising:
computing a gradient of the objective function;
setting the search direction along the gradient;
updating the search direction;
performing a golden section search to set a step size;
computing the gradient of the objective function based on the updated search direction and the step size;
updating material property vectors; and
comparing a value of the objective function based on the updated material property vector to the desired accuracy threshold.

15. The computer-readable storage media of claim 11, the acts further comprising:

mapping the volumetric material model to a virtual object volume;
assigning virtual illumination conditions to the virtual object volume; and
rendering the virtual object volume using the virtual illumination conditions as a boundary condition for a system of diffusion equations of the virtual object volume.

16. A method comprising:

capturing at least one image of a sample of a heterogeneous material illuminated by at least one illumination condition, the at least one illumination condition corresponding to the at least one image captured;

resolving, by a computing device, at least one volumetric material property of the heterogeneous material, the resolving comprises:

including a regularization term in a diffusion coefficient;
referencing data derived from the at least one image and the at least one illumination condition; and
solving an inverse diffusion problem by computing a gradient of an objective function associated with the inverse diffusion problem, setting a search direction along the gradient, setting a step size, and computing the gradient of the objective function based on the search direction and the step size.

17. The method of claim 16, wherein the computing the gradient of the objective function further comprises computing a gradient for at least one volumetric material property using a conjugate gradient based algorithm.

18. The method of claim 16, wherein the computing the gradient of the objective function further comprises computing a gradient for at least one volumetric material property using an adjoint method.

* * * * *